United States Patent
Chow et al.

(10) Patent No.: US 9,040,532 B2
(45) Date of Patent: May 26, 2015

(54) ALPHA ADRENERGIC RECEPTOR MODULATORS

(75) Inventors: Ken Chow, Newport Coast, CA (US); Liming Wang, Irvine, CA (US); Wenkui K. Fang, Irvine, CA (US); Evelyn G. Corpuz, Irvine, CA (US); Santosh C. Sinha, Ladera Ranch, CA (US); Daniel W. Gil, Corona Del Mar, CA (US); Mohammad I. Dibas, Laguna Niguel, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 433 days.

(21) Appl. No.: 13/500,501

(22) PCT Filed: Oct. 6, 2010

(86) PCT No.: PCT/US2010/051622
§ 371 (c)(1),
(2), (4) Date: May 1, 2012

(87) PCT Pub. No.: WO2011/044229
PCT Pub. Date: Apr. 14, 2011

(65) Prior Publication Data
US 2012/0208821 A1    Aug. 16, 2012

Related U.S. Application Data

(60) Provisional application No. 61/249,101, filed on Oct. 6, 2009.

(51) Int. Cl.
| | | |
|---|---|---|
| *A61K 31/40* | (2006.01) | |
| *A61K 31/498* | (2006.01) | |
| *A61K 31/4184* | (2006.01) | |
| *A61K 31/4709* | (2006.01) | |
| *C07D 403/12* | (2006.01) | |
| *C07D 401/12* | (2006.01) | |
| *C07D 207/22* | (2006.01) | |
| *C07D 409/12* | (2006.01) | |
| *C07D 413/12* | (2006.01) | |
| *C07D 417/12* | (2006.01) | |
| *C07D 471/04* | (2006.01) | |

(52) U.S. Cl.
CPC .......... *C07D 207/22* (2013.01); *C07D 403/12* (2013.01); *C07D 409/12* (2013.01); *C07D 413/12* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | |
|---|---|---|
| 3,636,219 A | 1/1972 | Culik |
| 3,890,319 A | 6/1975 | Danielewicz et al. |
| 4,515,800 A | 5/1985 | Cavero et al. |
| 4,587,257 A | 5/1986 | DeSantis et al. |
| 5,091,528 A | 2/1992 | Gluchowski |

FOREIGN PATENT DOCUMENTS

WO      WO 9200073      1/1992

OTHER PUBLICATIONS

Urosevic Dragan, et al., LNP 906, the first high-affinity photoaffinity ligand selective for I1 imidazoline receptors, British Journal of Pharmacology, Mar. 3, 2004, 609-617, 142.
Chapleo et al. "Heteroaromatic Analogues of the alpha.sub.2 -Adrenoreceptor Partial Agonist Clonidine" J. Med. Chem. 1989, 32, 1627-1630.
DeJong, et al, "Relationships Between Structure and a-Adrenergic Receptor Affinity of Clonidine and Some Related Cyclic Amidines", European Journal of Pharmacology. 69 (1981) 175-188.
Goldfarb, David Scott, "Method Using Lifespan-Altering Compounds for Altering the Lifespan of Eukaryotic Organisms, and Screening for Such Compounds", File CAPLUS XP-002619046, University of Rochester, USA, 2009.
S. A. Munk, "Analogs of UK 14,304: Structural Features Responsible for a 2 Adrenoceptor Activity", Bioorganic & Medicinal Chemistry Letters, vol. 5, No. 15. pr. 1745-1750, 1995.
Schann, et al.; "Synthesis and Biological Evaluation of Pyrrolinic Isosteres of Rilmenidine. Discovery of *cis-I trans-Dicyclopropylmethyl-(4,5-dimethyl-4,5-dihydro-3H*pyrrol-2-y1)-amine (LNP 509), an 1\ Imidazoline Receptor Selective Ligand with Hypotensive Activity", *J. Med. Chem.* 2001. 44. 1588-1593.

*Primary Examiner* — Savitha Rao
*Assistant Examiner* — Gregg Polansky
(74) *Attorney, Agent, or Firm* — Barbara C. Potts

(57) ABSTRACT

Compounds are described herein useful for treating diseases and conditions by modulation of one or more alpha adrenergic receptor. The compounds can include a naphthalene, a quinoline, a benzoimidazole or an isoquinoline as a core structure. Methods of making, using and formulating these compounds are described.

14 Claims, No Drawings

ALPHA ADRENERGIC RECEPTOR MODULATORS

CROSS REFERENCE TO RELATED APPLICATIONS

This is a national stage application under 35 U.S.C. 371 of PCT patent application PCT/U.S. Ser. No. 10/051,622, filed on Oct. 6, 2010, which claims the benefit of U.S. Provisional Application Ser. No. 61/249,101 filed on Oct. 6, 2009, each of which is hereby incorporated by reference in its entirety.

BACKGROUND OF THE INVENTION

Human adrenergic receptors are integral membrane proteins which have been classified into two broad classes, alpha and the beta adrenergic receptors. Both types of receptors mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds, forms one basis of classification: alpha receptors tend to bind norepinephrine more strongly than epinephrine. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha-1 ($\alpha_1$), alpha-2 ($\alpha_2$), beta-1 ($\beta_1$), and beta-2 ($\beta_2$) subtypes.

Alpha adrenergic agents are known in the art. Whereas alpha-1 agonists are known to include compounds which have vasoconstrictor activity and are thus useful for controlling intraocular bleeding, alpha-2 agonist are known to include compounds useful for reducing intraocular pressure (anti-glaucoma effect), for increasing renal flow (diuretics) and for altering the rate of fluid transport in the gastrointestinal tract (anti-diarrheals).

In "Heteroaromatic Analogues of the alpha.sub.2-Adrenoreceptor Partial Agonist Clonidine" J. Med. Chem. 1989, 32, 1627-1630, Chapleo et al. describe 6-(2-iminoimidazolidine)-3-oxo-3,4-dihydro-(2H)-1,4-benzoxazine and 7-(2-iminoimidazolidine)-3-oxo-3,4-dihydro-(2H)-1,4-benzoxazi compounds as partial alpha-2 agonists.

"Analogs of UK 14,304: Structural Features Responsible for α2 Andrenoceptor Activity", Bioorg. & Med. Chem. Letters, Vol 5, No. 15, pp 1745-1750 describes aminoimidazoline derivatives with α2 activity.

U.S. Pat. No. 3,890,319 discloses 2-imidazolin-2-yl-amino-substituted quinoxalines as regulators of the cardiovascular system.

U.S. Pat. No. 4,515,800, describes 2-(trisubstituted phenylimino)imidazoline compounds [also known as 2-(trisubstituted-anilino)-1,3-diazacyclopentene-(2) compounds] in pharmaceutical compositions, preferably in eye drops, for the treatment of glaucoma.

U.S. Pat. No. 4,587,257 discloses 2-(trisubstituted phenylimino)imidazoline compounds capable of controlling ocular bleeding.

U.S. Pat. No. 3,636,219 discloses 2-(substituted-phenylamino)-thiazolines and imidazolines having anticholinergic activity.

U.S. Pat. No. 5,091,528 discloses 6- or 7-(2-imino-2-imidazolidine)-1,4-benzoxazines as alpha adrenergic agents having alpha adrenergic activity and useful for the treatment of glaucoma, renal and gastrointestinal disorders and vasoconstrictors.

Compound (+/−) 3,4-dihydro-N-(1,2,3,4-tetrahydro-1-naphthalenyl)-2H-pyrrol-5-amine CAS 753464-99-2 is available from Aurora Screening Library.

Functional differences between alpha-1 and alpha-2 receptors have been recognized, and compounds which exhibit selective binding between these two subtypes have been developed. Thus, in WO 9200073 for example, the selective ability of the R(+) enantiomer of terazosin to selectively bind to adrenergic receptors of the alpha-1 subtype was reported. The alpha-1/alpha-2 selectivity of this compound was disclosed as being significant because agonist stimulation of the alpha-2 receptors was said to inhibit secretion of epinephrine and norepinephrine, while antagonism of the alpha-2 receptor was said to increase secretion of these hormones. Thus, the use of non-selective alpha-adrenergic blockers, such as phenoxybenzamine and phentolamine, was said to be limited by their alpha-2 adrenergic receptor mediated induction of increased plasma catecholamine concentration and the attendant physiological sequalae (increased heart rate and smooth muscle contraction).

The cloning, sequencing and expression of alpha receptor subtypes from animal tissues has led to the subclassification of the alpha-1 adrenoreceptors into alpha-1A, alpha-1B, and alpha-1D. Similarly, the alpha-2 adrenoreceptors have also been classified alpha-2A, alpha-2B, and alpha-2C receptors. Each alpha-2 receptor subtype appears to exhibit its own pharmacological and tissue specificities. Compounds having a degree of specificity for one or more of these subtypes may be more specific therapeutic agents for a given indication than an alpha-2 receptor pan-agonist (such as the drug clonidine) or a pan-antagonist.

Among other indications, such as the treatment of glaucoma, hypertension, sexual dysfunction, and depression, certain compounds having alpha adrenergic receptor agonist activity are known analgesics. However, many compounds having such activity do not provide the activity and specificity desirable when treating disorders modulated by alpha adrenoreceptors. For example, many compounds found to be effective agents in the treatment of pain are frequently found to have undesirable side effects, such as causing hypotension and sedation at systemically effective doses.

SUMMARY

Described herein are compounds that are useful as alpha adrenergic receptor modulators. These compounds are useful in treating a wide variety of disorders associated with modulation of alpha adrenergic receptors. These compounds are useful for the treatment of humans with diseases and conditions that are alleviated by alpha adrenergic modulation, and in particular, useful as alpha-1 and/or alpha-2 antagonists or agonists. Compositions are also described herein comprising a pharmaceutically acceptable amount of a compound as described herein. Further described are methods for treating conditions using the compositions described herein, wherein the conditions are selected from the group consisting of including but not limited to treating glaucoma, elevated intraocular pressure, ischemic neuropathies, optic neuropathy, pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, stroke, cognitive deficits, neuropsychiatric conditions, drug dependence and addiction, withdrawal symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, Parkinson's ALS, and other neurodegenerative diseases, dermatological conditions, skin erythema (redness) and inflammation, rosacea, acne, psoriasis, inflammatory bowel disease (IBD), post-traumatic stress disorder (PTSD), Tourette's syndrome, multiple sclerosis, dry eye disease.

Certain terms as used in the specification are intended to refer to the following definitions, as detailed below. Where the definition of terms departs from the commonly used meaning of the term, applicant intends to utilize the definitions provided below, unless specifically indicated.

DETAILED DESCRIPTION

In one aspect, the invention therefore provides a compound having formula I, its enantiomers, diastereoisomers, tautomers or a pharmaceutically acceptable salt thereof

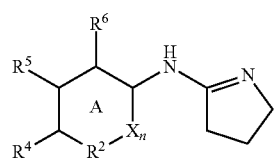

Formula I wherein:
n is 0 or 1;
A is an aromatic or non-aromatic ring;
X is N, N—$R^1$, CH—$R^1$, C—$R^1$;
$R^1$ is H, $C_{1-6}$ alkyl or halogen;
$R^2$ is N, N—$R^3$, CH—$R^3$, C—$R^3$, O or S;
$R^3$ is H, halogen, or $C_{1-6}$ alkyl;
$R^4$ is halogen, H, $C_{1-6}$ alkyl or part of a ring as a heteroatom (O, S, N) or as a C;
$R^5$ is a heteroatom (S, N) or is a C and is always part of a ring;
$R^6$ is H, $C_{1-6}$ alkyl, halogen or is part of a ring as a heteroatom (O, S, N) or as a C;
$R^4$ and $R^5$ can form a 5 or 6 membered carbo- or heterocyclic ring, aromatic or non-aromatic, optionally substituted with 1 to 2 $C_{1-6}$ alkyl or with 1 to 2 halogen and is directly attached to the rest of the molecule; or
$R^5$ and $R^6$ can form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule;
except (+/−) 3,4-dihydro-N-(1,2,3,4-tetrahydro-1-naphthalenyl)-2H-pyrrol-5-amine.

In another aspect, the invention therefore provides a compound having formula II, its enantiomers, diastereoisomers, tautomers or a pharmaceutically acceptable salt thereof

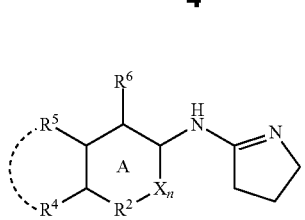

Formula II wherein:
n is 1;
A is an aromatic ring;
X is C—$R^1$;
$R^1$ is H;
$R^2$ is N or C—$R^3$;
$R^3$ is H, halogen, or $C_{1-6}$ alkyl;
$R^4$ is part of a ring as a heteroatom (O, S, N) or as a C;
$R^5$ is a heteroatom (N) or is a C and is always part of a ring;
$R^6$ is H, $C_{1-6}$ alkyl or halogen; and
$R^4$ and $R^5$ form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule.

In another aspect, the invention therefore provides a compound having formula III, its enantiomers, diastereoisomers, tautomers or a pharmaceutically acceptable salt thereof.

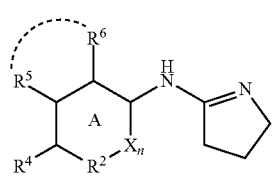

Formula III wherein:
n is 1;
A is an aromatic ring;
X is C—$R^1$;
$R^1$ is H, $C_{1-3}$ alkyl;
$R^2$ is N or C—$R^3$;
$R^3$ is H, halogen, or $C_{1-6}$ alkyl;
$R^4$ is halogen or H;
$R^5$ is a heteroatom (N) or C and is always part of a ring;
$R^6$ is part of a ring as a heteroatom (N) or as a C;
$R^5$ and $R^6$ can form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule.

In another aspect, the invention therefore provides a compound having formula IV, its enantiomers, diastereoisomers, tautomers or a pharmaceutically acceptable salt thereof

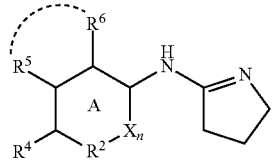

Formula IV wherein:
n is 0;
A is a non-aromatic ring;

R² is CH—R³;
R³ is H;
R⁴ is H;
R⁵ is C and is always part of a ring;
R⁶ is part of a ring as a C; and
R⁵ and R⁶ can form a 6 membered aromatic carbocyclic ring directly attached to the rest of the molecule.

In another aspect, the invention therefore provides a compound having formula V, its enantiomers, diastereoisomers, tautomers or a pharmaceutically acceptable salt thereof

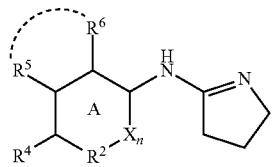

Formula V wherein
n is 1;
A is a non-aromatic ring;
X is CH—R¹;
R¹ is H;
R² is CH—R³.
R³ is H;
R⁴ is H;
R⁵ is C and is always part of a ring;
R⁶ is part of a ring as a C; and
R⁵ and R⁶ can form a 6 membered aromatic carbocyclic ring, optionally substituted with $C_{1-6}$ alkyl or halogen and is directly attached to the rest of the molecule; except (+/−) 3,4-dihydro-N-(1,2,3,4-tetrahydro-1-naphthalenyl)-2H-pyrrol-5-amine.

The person of skill in the art would appreciate that when "n" is 0 then X is absent and ring A is a 5 membered ring.

The person of skill in the art would appreciate the formation of bicyclic hetero- or carbocyclic rings, when R⁴ and R⁵ form a 5 or 6 aromatic or non-aromatic membered carbo- or heterocyclic ring, directly attached to the rest of the molecule.

The person of skill in the art would appreciate the formation of bicyclic hetero- or carbocyclic rings, when R⁵ and R⁶ form a 5 or 6 aromatic or non-aromatic membered carbo- or heterocyclic ring, directly attached to the rest of the molecule.

The person of skill in the art would appreciate that when "A" is an aromatic ring X is N or C—R¹ and when "A" is a non-aromatic ring X is N—R¹ or CH—R¹.

The person of skill in the art would appreciate that when "A" is an aromatic ring R² is N or C—R³ and when "A" is a non-aromatic ring R² is N—R³, O, S or CH—R³.

Further, pharmaceutically acceptable salts, hydrates, solvates, crystal forms and individual isomers, enantiomers, tautomers, diastereomers and prodrugs of the compounds described can be utilized.

The term "alkyl" as used herein, is defined as including a saturated monovalent hydrocarbon moiety having straight or branched moieties or combinations thereof and containing 1-6 carbon atoms, preferably 1-3 carbon atoms. Alkyl moieties can optionally be substituted by cycloalkyl groups or one methylene group (—CH₂—) can be replaced by carbonyl or carboxyl group. Usually, in the present case, alkyl group is methyl.

The term "cycloalkyl" as used herein, refers to a monovalent or divalent group of 3 to 8 carbon atoms, preferably 3-6 carbon atoms derived from saturated cyclic hydrocarbon. Cycloalkyl groups can be optionally substituted by alkyl groups or halogen groups. Usually, in the present case, cycloalkyl groups are cyclohexyl, cyclopentyl.

The term "halogen" as used herein includes an atom of fluoride, chloride, bromide or iodide. Usually, in the present case, halogens are fluoride, chloride and bromide.

The term "heterocyclic" ring as used herein, is defined as including an aromatic or non-aromatic moiety that includes at least one heteroatom in the ring, wherein one or more ring carbons are replaced with a heteroatom. Heterocyclic rings can have at least one O or N or S interrupting the cyclic ring structure or combinations thereof. In the present case heterocyclic rings can be aromatic or non aromatic and can be formed of 5 or 6 atoms. Heterocyclic ring moieties can be optionally substituted by alkyl or halogen groups, as defined above. Usually, in the present case, heterocyclic rings are imidazole, thiazol, morpholine, pyrrol, pyridine, pyrazine, furan, thiophene.

The term "bicyclic heterocyclic" rings as used herein, refers to aromatic or non-aromatic fused cyclic rings wherein at least one of the cycles has a heteroatom in its ring, as defined above. Usually, in the present case, bicyclic heterocyclic rings are quinoxaline, quinoline, isoquinoline, benzimidazole, benzothiazole, 3,4-dihydro-2H-benzo[b][1,4]oxazine, indole, 1 Hpyrrolo[2,3-b]pyridine, 6,7-dihydro-5H-cyclopenta[b]pyridine, 1,5-napthyridine, benzothiophene, benzofuran.

The term "carbocyclic" ring as used herein refers to a ring formed only by carbon atoms. In the present case carbocyclic rings can be aromatic or non aromatic and can be formed of 5 or 6 carbon atoms. Carbocyclic rings can optionally be substituted by alkyl or halogen, as defined above. Usually, in the present case, carbocyclic rings are phenyl, cyclohexyl, cyclopentyl.

The term "bicyclic carbocyclic" rings as used herein, refers to aromatic or non-aromatic fused carbocyclic rings formed only by carbon atoms. Usually, in the present case, bicyclic carbocyclic rings are naphthalene, tetrahydronaphtalene, dihydroindene.

The term "N" as used herein, refers to a nitrogen atom.
The term "O" as used herein, refers to an oxygen atom.
The term "S" as used herein, refers to a sulfur atom.
The term "H" as used herein, refers to a hydrogen atom.
The term "C" as used herein, refers to a carbon atom.

As used herein, "pharmaceutically acceptable salt" refers to any salt that retains the activity of the parent compound and does not impart any additional deleterious or untoward effects on the subject to which it is administered, and in the context in which it is administered compared to the parent compound. A pharmaceutically acceptable salt also refers to any salt which may form in vivo as a result of administration of an acid, another salt, or a prodrug which is converted into an acid or salt. Further, pharmaceutically acceptable salt refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, fumaric acid, salicylic acid and the like.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

As used herein "prodrug" refers to a compound which is converted to a therapeutically active compound after administration, and the term should be interpreted as broadly herein as is generally understood in the art. While not intending to limit the scope of the present description, conversion may occur by hydrolysis of an ester group or some other biologically labile group. Generally, but not necessarily, a prodrug is inactive or less active than the therapeutically active compound to which it is converted.

As used herein, "tautomer" refers to the migration of protons between adjacent single and double bonds. The tautomerization process is reversible. Compounds described herein can undergo any possible tautomerization that is within the physical characteristics of the compound.

The following is an example tautomerization that can occur in compounds described herein:

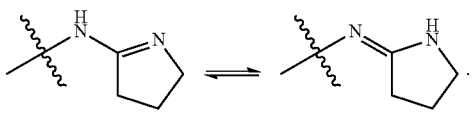 [SMILES: *NC1=NCCC1 ; */N=C1\CCCN1]

As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

Compounds of the invention are:
N-1-Naphthyl-3,4-dihydro-2H-pyrrol-5-amine;
N-(2-Methyl-1-naphthyl)-3,4-dihydro-2H-pyrrol-5-amine;
N-(4-Bromo-1-naphthyl)-3,4-dihydro-2H-pyrrol-5-amine;
N-(3,4-Dihydro-2H-pyrrol-5-yl)-1H-benzimidazol-5-amine;
N-(3,4-Dihydro-2H-pyrrol-5-yl)-6,7-dihydro-5H-cyclopenta[b]pyridin-3-amine;
4-Chloro-N-[(2E)-pyrrolidin-2-ylidene]-1,5-naphthyridin-3-amine;
N-(4-Chloro-1-naphthyl)-3,4-dihydro-2H-pyrrol-5-amine fumarate;
N-(4-Chloro-1-naphthyl)-3,4-dihydro-2H-pyrrol-5-amine;
5-Bromo-N-(3,4-dihydro-2H-pyrrol-5-yl)quinoxalin-6-amine fumarate;
5-Bromo-N-(3,4-dihydro-2H-pyrrol-5-yl)quinoxalin-6-amine;
8-Chloro-N-(3,4-dihydro-2H-pyrrol-5-yl)quinolin-7-amine;
4-Bromo-N-(3,4-dihydro-2H-pyrrol-5-yl)-1H-benzimidazol-5-amine;
4-Chloro-N-(3,4-dihydro-2H-pyrrol-5-yl)-1H-benzimidazol-5-amine;
N-(3,4-dihydro-2H-pyrrol-5-yl)-4-methyl-1H-benzimidazol-5-amine;
7-Chloro-N-(3,4-dihydro-2H-pyrrol-5-yl)-1H-benzimidazol-5-amine;
N-(3,4-Dihydro-2H-pyrrol-5-yl)quinoxalin-6-amine;
N-(5,6,7,8-Tetrahydronaphthalen-2-yl)-3,4-dihydro-2H-pyrrol-5-amine;
N-(2,3-Dihydro-1H-inden-4-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;
7-Bromo-N-(3,4-dihydro-2H-pyrrol-5-yl)-1H-indol-5-amine;
N-(3,4-Dihydro-2H-pyrrol-5-yl)-1H-indol-6-amine;
N-(3,4-Dihydro-2H-pyrrol-5-yl)-1H-indol-7-amine;
N-1-Benzothien-5-yl-3,4-dihydro-2H-pyrrol-5-amine;
N-1-Benzofuran-5-yl-3,4-dihydro-2H-pyrrol-5-amine;
N-(3,4-Dihydro-2H-pyrrol-5-yl)-1H-indol-4-amine;
N-[(2E)-Pyrrolidin-2-ylidene]-1H-pyrrolo[2,3-b]pyridin-5-amine;
N-(3,4-Dihydro-2H-pyrrol-5-yl)-5-methylquinoxalin-6-amine fumarate;
N-(3,4-Dihydro-2H-pyrrol-5-yl)-5-methylquinoxalin-6-amine;
N-(3,4-Dihydro-2H-pyrrol-5-yl)quinolin-7-amine;
N-(3,4-Dihydro-2H-pyrrol-5-yl)-8-methylquinolin-7-amine;
N-(3,4-Dihydro-2H-pyrrol-5-yl)-8-methylquinolin-7-amine fumarate;
N-(3,4-dihydro-2H-pyrrol-5-yl)quinolin-8-amine;
4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-(3,4-Dihydro-2H-pyrrol-5-yl)isoquinolin-8-amine fumarate;
N-(3,4-Dihydro-2H-pyrrol-5-yl)isoquinolin-8-amine;
N-[(1S)-2,3-Dihydro-1H-inden-1-yl]-3,4-dihydro-2H-pyrrol-5-amine;
N-[(1S)-1,2,3,4-Tetrahydronaphthalen-1-yl]-3,4-dihydro-2H-pyrrol-5-amine;
N-(7-Fluoro-2,3-dihydro-1H-inden-1-yl)-3,4-dihydro-2H-pyrrol-5-amine;
N-(3,4-Dihydro-2H-pyrrol-5-yl)-5-methyl-3,4-dihydro-2H-1,4-benzoxazin-6-amine;
N-[(1S)-4-Methyl-2,3-dihydro-1H-inden-1-yl]-3,4-dihydro-2H-pyrrol-5-amine;
4-Methyl-N-[(2E)-pyrrolidin-2-ylidene]-1H-pyrrolo[2,3-b]pyridin-5-amine.

Preferred compounds of the invention are:
N-1-Naphthyl-3,4-dihydro-2H-pyrrol-5-amine;
N-(3,4-Dihydro-2H-pyrrol-5-yl)-1H-benzimidazol-5-amine;
4-Bromo-N-(3,4-dihydro-2H-pyrrol-5-yl)-1H-benzimidazol-5-amine;
N-(5,6,7,8-Tetrahydronaphthalen-2-yl)-3,4-dihydro-2H-pyrrol-5-amine;
N-(2,3-Dihydro-1H-inden-4-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;
7-Bromo-N-(3,4-dihydro-2H-pyrrol-5-yl)-1H-indol-5-amine;
N-(3,4-Dihydro-2H-pyrrol-5-yl)-1H-indol-6-amine;
N-1-Benzothien-5-yl-3,4-dihydro-2H-pyrrol-5-amine;
N-(3,4-Dihydro-2H-pyrrol-5-yl)-1H-indol-4-amine;
N-[(2E)-Pyrrolidin-2-ylidene]-1H-pyrrolo[2,3-b]pyridin-5-amine;
N-(3,4-Dihydro-2H-pyrrol-5-yl)-5-methylquinoxalin-6-amine fumarate;

N-(3,4-Dihydro-2H-pyrrol-5-yl)-5-methylquinoxalin-6-amine;
N-(3,4-Dihydro-2H-pyrrol-5-yl)quinolin-7-amine;
N-(3,4-Dihydro-2H-pyrrol-5-yl)-8-methylquinolin-7-amine;
N-(3,4-Dihydro-2H-pyrrol-5-yl)-8-methylquinolin-7-amine fumarate;
4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-[(1S)-2,3-Dihydro-1H-inden-1-yl]-3,4-dihydro-2H-pyrrol-5-amine;
N-[(1S)-1,2,3,4-Tetrahydronaphthalen-1-yl]-3,4-dihydro-2H-pyrrol-5-amine.

Most preferred compounds of the invention are:
4-Bromo-N-(3,4-dihydro-2H-pyrrol-5-yl)-1H-benzimidazol-5-amine;
N-(5,6,7,8-Tetrahydronaphthalen-2-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;
7-Bromo-N-(3,4-dihydro-2H-pyrrol-5-yl)-1H-indol-5-amine;
N-1-Benzothien-5-yl-3,4-dihydro-2H-pyrrol-5-amine;
N-(3,4-Dihydro-2H-pyrrol-5-yl)-8-methylquinolin-7-amine fumarate;
4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-(3,4-Dihydro-2H-pyrrol-5-yl)-8-methylquinolin-7-amine.

The compounds described herein are useful as medicaments, or in compositions or formulations in mammals, including humans, for treatment of diseases and or alleviations of conditions which are responsive to treatment by modulation of alpha adrenergic receptors. Thus, in further embodiment examples, there are provided methods for treating a disorder associated with modulation of alpha adrenergic receptors. Such methods can be performed, for example, by administering to a subject in need thereof a pharmaceutical composition containing a therapeutically effective amount of at least one compound described herein.

The compounds described herein may be administered at pharmaceutically effective dosages. Such dosages are normally the minimum dose necessary to achieve the desired therapeutic effect. Generally, such doses will be in the range of about 1 mg/day to about 1000 mg/day; more preferably in the range of about 10 mg/day to about 500 mg/day. In another embodiment example, the compound or compounds may be present in a composition or formulation in a range of about 0.5 mg/kg/day to about 100 mg/kg/day or about 1 mg/kg/day to about 100 mg/kg/day. However, the actual amount of the compound to be administered in any given case will be determined by a physician taking into account the relevant circumstances, such as the severity of the pain, the age and weight of the patient, the patient's general physical condition, the cause of pain, and the route of administration.

In another aspect of the invention, provided are pharmaceutical compositions including at least one compound in a pharmaceutically acceptable carrier. Pharmaceutical compositions can be used in the form of a solid, a solution, an emulsion, a dispersion, a micelle, a liposome, and the like, wherein the resulting composition contains one or more compounds described herein, as an active ingredient, in admixture with an organic or inorganic carrier or excipient suitable for enteral or parenteral applications. One or more compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Compounds described herein are included in pharmaceutical compositions in an amount sufficient to produce the desired effect upon the process or disease condition.

In another aspect of the invention, the compounds described herein can be administered orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of drug released at a given time during the course of therapy.

Pharmaceutical compositions in a form suitable for oral use, for example, are administered as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients may also be manufactured by known methods.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the compounds are mixed with an inert solid diluent, for example, calcium carbonate, calcium phosphate or kaolin. They may also be in the form of soft gelatin capsules wherein the compounds are mixed with water or an oil medium, for example, peanut oil, liquid paraffin, or olive oil.

The pharmaceutical compositions may also be in the form of a sterile injectable suspension. Suspensions may be formulated according to known methods using suitable dispersing or wetting agents and suspending agents. The sterile injectable preparations may also be sterile injectable solutions or suspensions in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds described herein may also be administered in the form of suppositories for rectal administration. These compositions may be prepared by mixing the compounds with a suitable non-irritating excipient, such as cocoa butter, synthetic glyceride esters of polyethylene glycols, which are solid at ordinary temperatures, but liquefy and/or dissolve in the rectal cavity to release the drug.

The compounds described herein can also be administered as an ophthalmically acceptable formulation or composition. A liquid which is ophthalmically acceptable is formulated such that it can be administered topically to the eye. The comfort should be maximized as much as possible, although sometimes formulation considerations (e.g. stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in ophthalmic compositions described herein include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations described herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In another aspect of the invention, an ophthalmic composition as described herein may have ingredients used in the following amounts listed in Table 1.

TABLE 1

| Ingredient | Amount (% w/v) |
| --- | --- |
| active ingredient | about 0.001-5 |
| preservative | 0-0.10 |
| vehicle | 0-40 |

TABLE 1-continued

| Ingredient | Amount (% w/v) |
| --- | --- |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

In other embodiments, the ophthalmically acceptable liquid can be formulated for intraocular injection. The compounds described herein can be formulated as a liquid, gel paste, or the like for intraocular injection. Further, the compounds can be formulated into sustained release or controlled release intraocular implants comprising biodegradable polymers such as polylactic acid, poly glycolic acid, combinations thereof and the like.

Since individual subjects may present a wide variation in severity of symptoms and each composition has its unique therapeutic characteristics, the precise mode of administration and dosage employed for each subject is left to the discretion of the practitioner.

EXPERIMENTAL DETAILS

The present invention concerns also a process for preparing the compounds having formulae I, II, III, IV or V.

The synthetic schemes set forth below, illustrate how compounds according to the invention can be made. Those skilled in the art will be able to routinely modify and/or adapt the following schemes to synthesize any compounds of the invention covered by formulae I, II, III, IV or V.

Pyrrol-amines can be obtained according to the following general schemes. Most of the primary amine are commercially available. In Scheme 1 the primary amine reacts with pyrrolidin-2-one in the presence of phosphoryl chloride to form the desired pyrrol-amine. The solvent for this reaction is toluene.

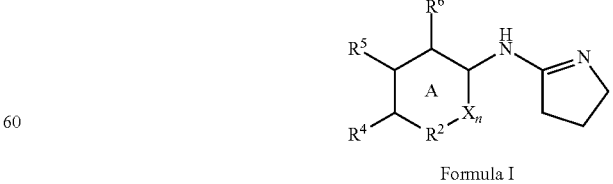

Scheme 1

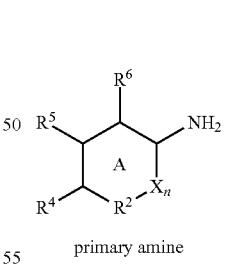

primary amine

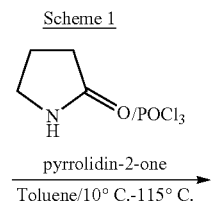

Formula I

In Scheme 2 the primary amine reacts with 5-(methylthio)-3,4-dihydro-2H-pyrrole in isopropanol to form the desired pyrrol-amine.

Scheme 2

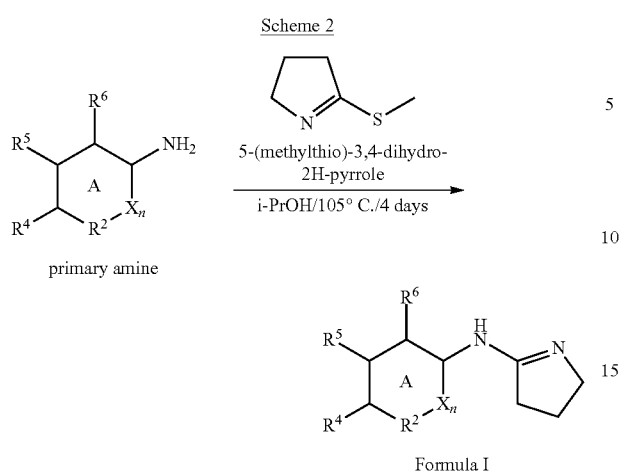

Formula I

In Scheme 3 the primary amine reacts with 5-methoxy-3,4-dihydro-2H-pyrrole in methanol to form the desired pyrrolamine.

Scheme 3

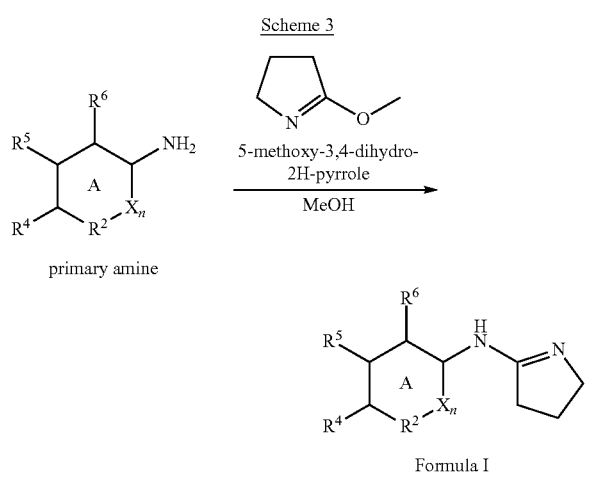

Formula I

The following examples are for illustrative purposes only and are not intended, nor should they be construed as limiting the invention in any manner. Those skilled in the art will appreciate that variations and modifications of the following examples can be made without exceeding the spirit or scope of the invention.

The IUPAC names of the compounds mentioned in the examples were generated with ACD version 8.

Unless specified otherwise in the examples, characterization of the compounds is performed according to the following methods:

NMR spectra are recorded on 300 MHz Varian and acquired at room temperature. Chemical shifts are given in p.p.m. referenced either to internal TMS or to the residual solvent signal.

All the reagents, solvents, catalysts for which the synthesis is not described are purchased from chemical vendors such as Sigma Aldrich, Fluka, Lancaster, however some known reaction intermediates, for which the CAS registry number (CAS) are mentioned, were prepared in-house following known procedures.

Usually the compounds of the invention were purified by flash column chromatography using as solvent system: 7N $NH_3$ in MeOH/DCM.

The following abbreviations are used in the examples:
$POCl_3$ phosphoryl chloride
DCM dichloromethane
NaOH sodium hydroxide
MeOH methanol
$CD_3OD$ deuterated methanol
$NH_3$ ammonia
EtOAc ethylacetate
Pd/C palladium on carbon
$H_2SO_4$ sulfuric acid
$Na_2SO_4$ sodium sulfate
$Bu_4NNO_2$ tetrabutylammonium nitrate
$Ac_2O$ trifluoroacetic anhydride
DMF dimethylformamide
$MgSO_4$ magnesium sulfate
EtOAc ethylacetate
i-PrOH isopropanol
NaI sodium iodide
$CDCl_3$ deuterated chloroform
AcOH acetic acid
MPLC medium pressure liquid chromatography

EXAMPLE 1

N-1-Naphthyl-3,4-dihydro-2H-pyrrol-5-amine

Compound 1

A solution of $POCl_3$ (765 mg) in 8 mL of toluene was added slowly to a solution of 2-pyrrolidinone (85 g) in 8 mL of toluene at 10° C. Then, the reaction was stirred at room temperature for 3 hours. A solution of 1-naphthylamine (858 mg) (CAS 134-32-7) in 8 mL of toluene was added, and the mixture was heated to reflux overnight. The refluxed mixture was cooled to room temperature, and the toluene layer was decanted. The residue was dissolved in aqueous water and DCM. Aqueous 5N NaOH was used to adjust the pH to alkaline. Two layers were separated, and the organic layer was washed with water and brine, dried over $Na_2SO_4$ and concentrated under reduced vacuum. Flash column chromatography (2-4% 7N $NH_3$ in MeOH/DCM) yielded the title compound. $^1$H NMR (300 MHz, $CD_3OD$) 2.09 (m, 2H), 2.61 (m, 2H), 3.86 (m, 2H), 7.27 (m, 1H), 7.45 (m, 1H), 7.57 (m, 2H), 7.87 (m, 2H), 7.99 (m, 1H).

Compounds 2, 3, 4, 5 and 6 were prepared in a similar manner to the method described in Example 1 for Compound 1. The reagents used and the results obtained are tabulated below in Table 2.

TABLE 2

| Compound Number | IUPAC Name | Starting material | $^1$H NMR (Solvent) δ ppm |
|---|---|---|---|
| 2 | N-(2-Methyl-1-naphthyl)-3,4-dihydro-2H-pyrrol-5-amine | 1-amino-2-methylnaphtalene (CAS 2246-44-8) | ($CD_3OD$) 2.12 (m, 2H), 2.29 (s, 3H), 2.81 (m, 2H), 3.33 (m, 2H), 7.37 (m, 3H), 7.55 (d, J = 8.21 Hz, 1H), 7.77 (m, 1H), 7.85 (m, 1H). |
| 3 | N-(4-Bromo-1-naphthyl)-3,4-dihydro-2H-pyrrol-5-amine | 1-amino-4-bromonaphtalene (CAS 2298-07-9) | ($CD_3OD$) 2.08 (m, 2H), 2.62 (m, 2H), 3.36 (t, J = 6.74 Hz, 2H), 6.90 (d J = 7.91 Hz, 1H), 7.50 (dd, J = 1.17 & 7.30 Hz 1H), 7.55 (dd, J = 1.17 & 8.20 Hz, 1H), 7.70 (d, J = 7.91 Hz, 1H), 8.00 (dd, J = 0.80 & 8.50 Hz, 1H), 8.15 (dd, J = 0.80 & 8.20 Hz, 1H). |

TABLE 2-continued

| Compound Number | IUPAC Name | Starting material | $^1$H NMR (Solvent) δ ppm |
|---|---|---|---|
| 4 | N-(3,4-Dihydro-2H-pyrrol-5-yl)-1H-benzimidazol-5-amine | 6-amino-1H-benzimidazole (CAS 934-22-5) | (CD$_3$OD) 2.05 (m, 2H), 2.57 (t, J = 7.92 Hz, 2H), 3.44 (t, J = 6.77 Hz, 2H), 6.90 (dd, J = 8.50 Hz & 1.76 Hz, 1 H), 7.25 (d, J = 1.76 Hz, 1H), 7.53 (d, J = 8.50 Hz, 1H), 7.90 (s, 1H). |
| 5 | N-(3,4-Dihydro-2H-pyrrol-5-yl)-6,7-dihydro-5H-cyclopenta[b]pyridin-3-amine | 6,7-dihydro-5H-cylopenta[b]pyridin-3-amine (CAS 178209-29-5) | (CD$_3$OD) 7.91 (br. s., 1H), 7.34 (br. s., 1H), 3.46 (t, J = 6.7 Hz, 2H), 2.92 (q, J = 7.4 Hz, 4H), 2.56 (t, J = 7.9 Hz, 2H), 1.97-2.24 (m, 2H). |
| 6 | 4-Chloro-N-[(2E)-pyrrolidin-2-ylidene]-1,5-naphthyridin-3-amine | 4-chloro-1,5-naphthyridin-3-amine (CAS 930276-73-6) | (CD$_3$OD) 8.88-8.99 (m, 1H), 8.64 (s, 1H), 8.41 (dd, J = 8.5, 1.2 Hz, 1H), 7.72 (dd, J = 8.5, 4.4 Hz, 1H), 3.46 (t, J = 6.9 Hz, 2H), 2.68 (br. s., 2H), 2.15 (quin, 2H). |

EXAMPLE 2

N-(4-Chloro-1-naphthyl)-3,4-dihydro-2H-pyrrol-5-amine

Compound 7

A solution of POCl$_3$ (382 mg) in 8 mL of toluene was added slowly to a solution of 2-pyrrolidinone (430 mg) in 8 mL of toluene at 10° C. Then, the reaction was stirred at room temperature for 3 hours. A solution of 4-chloro-1-naphthalenamine (CAS 4684-12-2) (533 mg) in 8 mL of toluene was added, and the refluxed mixture was then cooled to room temperature, and the toluene layer was decanted. The residue was dissolved in aqueous water and DCM. Aqueous 5N NaOH was used to adjust the pH to alkaline. The resulting two layers were separated, and the organic layer was washed with water and brine, dried over Na$_2$SO$_4$ and concentrated under reduced vacuum. Flash column chromatography (24% 7N NH$_3$ in MeOH/DCM) yielded the title compound. $^1$H NMR (300 MHz, CD$_3$OD) δ 2.11 (m, 2H), 2.66 (m, 2H), 3.36 (t, J=6.74 Hz, 2H), 6.96 (d J=7.91 Hz, 1H), 7.49 (m, 2H), 7.50 (dd, J=1.13 & 7.11 Hz, 1H), 8.00 (d, J=8.20 Hz, 1H), 8.20 (d, J=8.50 Hz, 1H). The fumarate salt of the tile compound was further obtained by crystallization with fumaric acid in ethanol. $^1$H NMR (300 MHz, CD$_3$OD) δ 8.34 (dd, J=7.2, 1.9 Hz, 1H), 8.01-8.08 (m, 1H), 7.65-7.79 (m, 3H), 7.41 (d, J=7.9 Hz, 1H), 6.66 (s, 1H), 3.51-3.66 (m, 3H), 3.07 (t, J=6.7 Hz, 2H), 2.28 (dq, 2H). Ratio: Free base:Fumaric acid=1:0.5.

Compound 8 and its fumarate salt were prepared in a similar manner to the method described in Example 2 for Compound 7. The reagent used and the results obtained are tabulated below in Table 3.

TABLE 3

| Compound Number | IUPAC Name | Starting material | $^1$H NMR (Solvent) δ ppm |
|---|---|---|---|
| 8 | 5-Bromo-N-(3,4-dihydro-2H-pyrrol-5-yl)quinoxalin-6-amine | 6-amino-5-bromoquinoxaline (CAS 50358-63-9) | Free base: (CD$_3$OD) 8.16 (d, J = 8.5 Hz, 1H), 8.01 (d, J = 8.5 Hz, 1H), 7.70 (d, J = 7.9 Hz, 1H), 7.54-7.63 (m, 1H), 7.44-7.54 (m, 1H), 6.90 (d, J = 7.9 Hz, 1H), 3.36 (t, J = 6.7 Hz, 2H), 2.63 (t, J = 7.5 Hz, 2H), 2.08 (qd, 2H). Fumarate salt: (CD$_3$OD) 8.29 (d, J = 7.91 Hz, 1H), 8.01 (d, J = 7.91 Hz, 1H), 7.88 (d, J = 8.20 Hz, 1H), 7.67-7.33 (m, 2H), 7.33 (d, J = 8.20 Hz, 1H), 6.66 (s, 1H), 3.59 (t, J = 6.7 Hz, 2H), 3.05 (t, J = 7.5 Hz, 2H), 2.29-2.24(m, 2H). Free base:Fumaric acid = 1:1 |

EXAMPLE 3

8-Chloro-N-(3,4-dihydro-2H-pyrrol-5-yl)quinolin-7-amine

Compound 9

To a mixture of 2-chlorobenzene-1,3-diamine (24 mmol) (CAS 6400-14-2) and NaI (150 mg) in 80% H$_2$SO$_4$ (20 g) was added Glycerol (45 g). The mixture was stirred at 150° C. to 170° C. for 5 h. The mixture was cooled to room temperature. Aqueous 5N NaOH was used to adjust the pH to alkaline, which was then extracted with EtOAc washed with brine, dried over MgSO$_4$ and concentrated under reduced vacuum. Flash column chromatography (EtOAc:Hexane) yielded 7-amino-8-chloroquinoline (800 mg), as a pale yellow solid. $^1$H NMR (300 MHz, CD$_3$OD) δ: 8.69 (dd, J=4.4, 1.8 Hz, 1H), 8.13 (dd, J=7.9, 1.8 Hz, 1H), 7.61 (d, J=9.1 Hz, 1H), 7.14-7.29 (m, 2H)

A solution of POCl$_3$ (551 mg) in 8 mL of toluene was added slowly to a solution of 2-pyrrolidinone (612 mg) in 8 mL of toluene at 10° C. Then the reaction was stirred at room temperature for 3 hours. A solution of 7-amino-8-chloroquinoline (760 mg) in 8 mL of toluene was added, and the mixture was heated to reflux for two hours. The refluxed mixture was then cooled to room temp, and the toluene layer was decanted. The residue was dissolved in water and DCM. Aqueous 5N NaOH was used to adjust the pH to alkaline. The two layers were separated, and the organic layer was washed with water and brine, dried over Na$_2$SO$_4$ and concentrated under reduced vacuum. Flash column chromatography (2-4% 7N NH$_3$ in MeOH/DCM) yielded the title compound. $^1$H NMR (300 MHz, CD$_3$OD) δ: 2.11 (m, 2H), 2.61 (m, 2H), 3.43 (t, J=6.74 Hz, 2H), 7.31 (d, J=8.50 Hz, 1H), 7.60 (dd, J=4.60 Hz & 8.20 Hz, 1H), 7.81 (d, J=8.70 Hz, 1H), 8.31 (dd, J=1.76 Hz & 8.20 Hz, 1H), 8.84 (dd, J=1.47 Hz & 4.40 Hz, 2H).

EXAMPLE 4

4-Bromo-N-(3,4-dihydro-2H-pyrrol-5-yl)-1H-benzimidazol-5-amine

Compound 10

5-(methylthio)-3,4-dihydro-2H-pyrrole (238 mg) was combined with of 1H-benzimidazol-6-amine, 7-bromo (430 mg) (CAS 177843-26-4) in 10 mL of isopropyl alcohol. The reaction was stirred at reflux for 4 days. The refluxed mixture was then cooled to room temperature and concentrated. Flash column chromatography (4-6% 7N NH$_3$ in MeOH/DCM) yielded the title compound $^1$H NMR (300 MHz, CD$_3$OD) δ 2.08 (m, 2H), 2.55 (t, J=7.92 Hz, 2H), 3.39 (t, J=6.74 Hz, 2H), 6.93 (d, J=8.50 Hz, 1H), 7.50 (d, J=8.50 Hz, 1H), 8.11 (s, 1H).

Compounds 11 to 26 were prepared in a similar manner to the method described in Example 4 for Compound 10. The reagents used and the results obtained are tabulated below in Table 4.

TABLE 4

| Compound Number | IUPAC Name | Starting material | $^1$H NMR (Solvent) δ ppm |
|---|---|---|---|
| 11 | 4-Chloro-N-(3,4-dihydro-2H-pyrrol-5-yl)-1H-benzimidazol-5-amine | 7-chloro-1H-benzimidazole-6-amine (CAS 177843-29-7) | (CD$_3$OD) 2.08 (m, 2H), 2.56 (t, J = 7.92 Hz, 2H), 3.40 (t, J = 6.74 Hz, 2H), 6.93 (d, J = 8.50 Hz, 1H), 7.46 (d, J = 8.50 Hz, 1H), 8.12 (s, 1H). |
| 12 | N-(3,4-dihydro-2H-pyrrol-5-yl)-4-methyl-1H-benzimidazol-5-amine | 7-methyl-1H-benzimidazole-6-amine (CAS 177843-30-0) | (CD$_3$OD) 2.09 (m, 2H), 2.62 (t, J = 7.92 Hz, 2H), 3.40 (t, J = 6.74 Hz, 2H), 6.87 (d, J = 8.50 Hz, 1H), 7.39 (d, J = 8.50 Hz, 1H), 8.07 (s, 1H). |
| 13 | 7-Chloro-N-(3,4-dihydro-2H-pyrrol-5-yl)-1H-benzimidazol-5-amine | 1H-Benzimidazol-5-amine, 7-chloro- (CAS 10597-54-3) | (CD$_3$OD) 2.06 (m, 2H), 2.61 (t, J = 7.92 Hz, 2H), 3.48 (t, J = 6.74 Hz, 2H), 7.01 (d, J = 1.47 Hz, 1H), 7.23 (d, J = 1.47 Hz, 1H), 8.12 (s, 1H). |
| 14 | N-(3,4-Dihydro-2H-pyrrol-5-yl)quinoxalin-6-amine | 6-aminoquinoxaline (CAS 6298-37-9) | (CDCl$_3$) 2.28 (m, 2H), 3.10 (t, J = 7.92 Hz, 2H), 3.83 (t, J = 7.33 Hz, 2H), 7.76 (dd, J = 2.45 Hz & 8.64 Hz, 1 H), 7.88 (d, J = 2.44 Hz, 1H), 8.15 (d, J = 8.64 Hz, 1H), 8.87 (dd, J = 1.72 Hz & 8.55 Hz, 2H). |
| 15 | N-(5,6,7,8-Tetrahydronaphthalen-2-yl)-3,4-dihydro-2H-pyrrol-5-amine | 8-aminoquanonoline (CAS 2217-41-6) | (CDCl$_3$) 7.48 (d, J = 7.9 Hz, 1H), 7.12 (t, J = 7.8 Hz, 1H), 6.96 (d, J = 7.3 Hz, 1H), 3.40 (t, J = 6.2 Hz, 2H), 2.78 (t, J = 6.0 Hz, 2H), 2.57 (t, J = 6.0 Hz, 4H), 2.04 (s, 4H), 2.01 (d, J = 5.9 Hz, 3H), 1.69-1.91 (m, 5H). |
| 16 | N-(2,3-Dihydro-1H-inden-4-yl)-3,4-dihydro-2H-pyrrol-5-amine | 1H-Inden-4-amine, 2,3-dihydro- (CAS 32202-61-2) | (CDCl$_3$)7.03-7.14 (m, 1H), 6.89 (d, J = 7.6 Hz, 2H), 3.47 (m, 2H), 2.92 (t, J = 7.5 Hz, 2H), 2.76 (t, J = 7.5 Hz, 2H), 2.53 (t, J = 7.6 Hz, 2H), 1.93-2.14 (m, 4H). |
| 17 | N-(3,4-Dihydro-2H-pyrrol-5-yl)-1H-indol-5-amine | 1H-Indol-5-amine (CAS 5192-03-0) | (CDCl$_3$) 7.24-7.34 (m, 2H), 7.16 (d, J = 3.2 Hz, 1H), 6.88 (dd, J = 8.5, 2.1 Hz, 1H), 6.46 (d, J = 3.2 Hz, 1H), 3.39-3.51 (m, 2H), 2.57 (t, J = 7.9 Hz, 2H), 2.05 (qd, 2H) |
| 18 | N-(3,4-Dihydro-2H-pyrrol-5-yl)-4-methyl-1H-indol-5-amine | 1H-Indol-5-amine, 4-methyl- (CAS 196205-06-8) | (CDCl$_3$) 7.11-7.18 (m, 2H), 6.80 (d, J = 8.5 Hz, 1H), 6.50 (d, J = 3.2 Hz, 1H), 3.37 (t, J = 6.7 Hz, 2H), 2.53 (t, J = 7.9 Hz, 2H), 2.36 (s, 3H), 2.06 (s, 3H). |
| 19 | N-(3,4-Dihydro-2H-pyrrol-5-yl)-7-methyl-1H-indol-5-amine | 1H-Indol-5-amine, 7-methyl (CAS 90868-09-0) | (CD$_3$OD) 7.17 (d, J = 3.2 Hz, 1H), 7.11 (d, J = 1.5 Hz, 1H), 6.67 (s, 1H), 6.35 (d, J = 3.2 Hz, 1H), 3.45 (t, J = 6.9 Hz, 2H), 2.57 (t, J = 7.9 Hz, 2H), 2.45 (s, 3H), 2.01 (quin, 2H). |
| 20 | 7-Bromo-N-(3,4-dihydro-2H-pyrrol-5-yl)-1H-indol-5-amine | 1H-Indol-5-amine, 7-bromo- (CAS 196205-07-9) | (CDCl$_3$) 7.25 (d, J = 3.2 Hz, 1H), 7.20 (d, J = 1.8 Hz, 1H), 7.04 (d, J = 1.8 Hz, 1H), 6.45 (d, J = 3.2 Hz, 1H), 3.44 (t, J = 6.9 Hz, 2H), 2.57 (t, J = 8.1 Hz, 2H), 2.03 (quin, 2H). |

TABLE 4-continued

| Compound Number | IUPAC Name | Starting material | $^1$H NMR (Solvent) δ ppm |
|---|---|---|---|
| 21 | N-(3,4-Dihydro-2H-pyrrol-5-yl)-1H-indol-6-amine | 1H-Indol-6-amine (CAS 5318-27-4) | (CDCl$_3$) 7.52 (d, J = 8.5 Hz, 1H), 7.18-7.31 (m, 1H), 7.11 (d, J = 3.2 Hz, 1H), 6.75 (dd, J = 8.4, 1.9 Hz, 1H), 6.48 (d, J = 4.1 Hz, 1H), 3.43-3.56 (m, 2H), 2.58 (t, J = 7.9 Hz, 2H), 2.10-2.03 (m, 2H). |
| 22 | N-(3,4-Dihydro-2H-pyrrol-5-yl)-1H-indol-7-amine | 1H-Indol-7-amine (CAS 5192-04-1) | (CD$_3$OD) 7.22-7.30 (m, 1H), 7.17 (d, J = 3.2 Hz, 1H), 6.93 (t, J = 7.6 Hz, 1H), 6.69 (d, J = 7.3 Hz, 1H), 6.41 (d, J = 3.2 Hz, 1H), 3.39 (t, J = 7.9 Hz, 2H), 2.62 (t, J = 7.9 Hz, 2H), 2.07 (quin, 2H). |
| 23 | N-1-Benzothien-5-yl-3,4-dihydro-2H-pyrrol-5-amine | Benzo[b]thiophen-5-amine (CAS 20532-28-9) | (CDCl$_3$) 7.75 (d, J = 8.5 Hz, 1H), 7.47 (br. s., 1H), 7.40 (d, J = 5.6 Hz, 1H), 7.20-7.30 (m, 1H), 7.01 (dd, J = 8.5, 2.1 Hz, 1H), 3.38-3.53 (m, 2H), 2.57 (t, J = 7.9 Hz, 2H), 2.07 (qd, 2H). |
| 24 | N-1-Benzofuran-5-yl-3,4-dihydro-2H-pyrrol-5-amine | 5-Benzofuranamine (CAS 58546-89-7) | (CDCl$_3$) 7.57 (d, J = 2.3 Hz, 1H), 7.39 (d, J = 8.8 Hz, 1H), 7.20-7.30 (m, 1H), 6.92 (dd, J = 8.6, 2.2 Hz, 1H), 6.68 (d, J = 2.1 Hz, 1H), 3.45 (t, J = 6.6 Hz, 2H), 2.55 (t, J = 8.1 Hz, 2H), 2.06 (quin, 2H). |
| 25 | N-(3,4-Dihydro-2H-pyrrol-5-yl)-1H-indol-4-amine | 1H-Indol-4-amine (CAS 5192-23-4) | (CD$_3$OD) 6.96-7.18 (m, 3H), 6.63-6.75 (m, 1H), 6.37 (d, J = 3.2 Hz, 1H), 3.42 (t, J = 6.9 Hz, 2H), 2.62 (t, J = 7.9 Hz, 2H), 1.96-2.18 (m, 2H). |
| 26 | N-[(2E)-Pyrrolidin-2-ylidene]-1H-pyrrolo[2,3-b]pyridin-5-amine | 3H-Pyrrolo[2,3-b]pyridin-5-amine (CAS 1187421-28-8) | (CD$_3$OD) 7.90 (d, J = 2.1 Hz, 1H), 7.65 (d, J = 2.1 Hz, 1H), 7.33 (d, J = 3.5 Hz, 1H), 6.39 (d, J = 3.5 Hz, 1H), 3.43 (t, J = 6.9 Hz, 2H), 2.57 (t, J = 7.9 Hz, 2H), 2.03 (quin, 2H). |

EXAMPLE 5

N-(3,4-Dihydro-2H-pyrrol-5-yl)-5-methylquinoxalin-6-amine

Compound 27

5-(methylthio)-3,4-dihydro-2H-pyrrole (260 mg) was combined with 5-methyl-6-quinoxalinamine, (360 mg) (CAS 171102-36-6) in 10 mL of isopropyl alcohol. The reaction was stirred at reflux for 2 days. The refluxed mixture was then cooled to room temperature and concentrated. Flash column chromatography (4-6% 7N NH$_3$ in MeOH/DCM) yielded the title compound. $^1$H NMR (300 MHz, CD$_3$OD) δ 2.34 (m, 2H), 2.75 (m, 3H), 3.16 (t, J=7.92 Hz, 2H), 3.71 (t, J=7.33 Hz, 2H), 7.75 (d, J=8.79 Hz, 1H), 8.07 (d, J=8.79 Hz, 1H), 8.95 (dd, J=1.76 Hz & 13.49 Hz, 2H). The fumarate salt of the title compound was further obtained by crystallization with fumaric acid from ethanol. $^1$H NMR (300 MHz, CD$_3$OD) δ 8.95 (dd, J=13.5, 1.8 Hz, 2H), 8.07 (d, J=8.5 Hz, 1H), 7.75 (d, J=8.8 Hz, 1H), 6.66 (s, 2H), 3.72 (t, J=7.2 Hz, 2H), 3.16 (t, J=8.1 Hz, 2H), 2.75 (s, 3H), 2.21-2.44 (m, 2H). Free base: Fumaric acid=1:1.

Compounds 28 to 31 and their corresponding fumarate salt were prepared in a similar manner to the method described in Example 5 for Compound 27. The reagents used and the results obtained are tabulated below in Table 5.

TABLE 5

| Compound Number | IUPAC Name | Starting material | $^1$H NMR (Solvent, δ ppm) |
|---|---|---|---|
| 28 | N-(3,4-Dihydro-2H-pyrrol-5-yl)quinolin-7-amine | 7-Quinolinamine (CAS 580-19-8) | (CDCl$_3$) 2.09 (m, 2H), 2.62 (m, 2H), 3.47 (m, 2H), 7.26 (m, 2H), 7.59 (d, J = 1.64 Hz, 1H), 7.32 (d, J = 8.79 Hz, 1H), 8.05 (dd, J = 1.76 Hz & 8.05 Hz, 1H), 8.81 (dd, J = 1.76 Hz & 4.10 Hz, 2H). |
| 29 | N-(3,4-Dihydro-2H-pyrrol-5-yl)-8-methylquinolin-7-amine | 7-amino-8-methylquinoline (CAS 116632-62-3) | Free base (CD$_3$OD) 2.33 (m, 2H), 2.74 (s, 3H), 3.15 (m, 2H), 3.71 (t, J = 7.33 Hz, 2H), 7.51 (d, J = 8.8 Hz, 1H), 7.60 (dd, J = 4.60 Hz & 8.32 Hz, 1H), 7.93 (d, J = 8.80 Hz, 1H), 8.38 (dd, J = 1.47 Hz & 8.31 Hz, 1H), 8.97 (dd, J = 1.47 Hz & 4.16 Hz, 2H). Fumarate salt (CD$_3$OD) 8.97 (dd, J = 4.2, 1.7 Hz, 1H), 8.38 (dd, J = 8.2, 1.6 Hz, 1H), 7.94 (d, J = 8.6 Hz, 1H), 7.60 (dd, J = 8.2, 4.3 Hz, 1H), 7.52 (d, J = 8.6 Hz, 1H), 6.66 (s, 2H), 3.71 (t, J = 7.1 Hz, 3H), 3.17 (br. s., 3H), 2.74 (s, 3H), 2.34 (quin, 2H). Free base:Fumaric acid = 1:1 |
| 30 | N-(3,4-dihydro-2H-pyrrol-5-yl)quinolin-8-amine | 8-aminoquanonoline (CAS 578-66-5) | Free base (CD$_3$OD) 2.33 (m, 2H), 3.22 (t, J = 8.20 Hz, 2H), 3.72 (t, J = 7.33 Hz, 2H), 7.65 (m, 1H), 7.72 (d J = 7.62 Hz, 1H), 7.85 (dd, J = 1.17 Hz & 7.33 Hz, 1H), 8.03 (dd, J = 1.47 Hz & 8.50 Hz, 1H), 8.46 (dd, J = 1.17 Hz & 8.21 Hz, 1H), 8.97 (dd, 1.76 Hz & 4.40 Hz, 1H). Fumarate salt (CD$_3$OD) 8.96 (dd, J = 4.3, 1.6 Hz, 1H), 8.46 (dd, J = 8.4, 1.3 Hz, 1H), 7.99-8.10 (m, 1H), 7.79-7.89 (m, 1H), 7.59-7.77 (m, 2H), 6.67 (s, 2H), 3.72 (t, J = 7.2 Hz, 2H), 3.22 (t, J = 8.2 Hz, 2H), 2.33 (quin, 2H). Free base:Fumaric acid = 1:1 |
| 31 | 4-Bromo-N-(3,4-dihydro-2H-pyrrol-5-yl)-1,3-benzothiazol-5-amine | 5-Benzothiazolamine, 4-bromo- (CAS 769-19-7) | Free base (CD$_3$OD) 9.43 (s, 1H), 8.22 (d, J = 8.5 Hz, 1H), 7.56 (d, J = 8.5 Hz, 1H), 6.68 (s, 2H), 3.71 (t, J = 7.3 Hz, 2H), 3.13 (t, J = 7.9 Hz, 2H), 2.23-2.43 (m, 2H). Fumarate salt (CD$_3$OD) 9.43 (s, 1H), 8.22 (d, J = 8.5 Hz, 1H), 7.56 (d, J = 8.5 Hz, 1H), 6.68 (s, 2H), 3.71 (t, J = 7.3 Hz, 2H), 3.13 (t, J = 7.9 Hz, 2H), 2.23-2.43 (m, 2H). Free base:Fumaric acid = 1:1 |

EXAMPLE 6

N-(3,4-Dihydro-2H-pyrrol-5-yl)isoquinolin-8-amine

Compound 32

5-Methoxy-3,4-dihydro-2H-pyrrole (220 mg) was combined with 8-isoquinolinamine (320 mg) (CAS 23687-27-6) in 10 mL of methanol in the presence of catalytic amount of AcOH. The reaction was stirred at 70° C. for 18 hours. The reaction was then cooled to room temperature and concentrated. Flash column chromatography (2-4% 7N NH$_3$ in MeOH/DCM) yielded the title compound. $^1$H NMR (300 MHz, CD$_3$OD) δ: 2.33 (m, 2H), 3.20 (m, 2H), 3.70 (t, J=3.33 Hz, 2H), 7.72 (dd, J=0.88 Hz & 7.33 Hz, 1H), 7.89 (t, J=7.33 Hz, 1H), 7.95 (dd, J=0.88 Hz & 5.86 Hz, 1H), 8.04 (d, J=8.50 Hz, 1H), 8.58 (d, J=5.86 Hz, 1H), 9.39 (d, J=0.88 Hz, 1H).

EXAMPLE 7

N-[(1S)-2,3-Dihydro-1H-inden-1-yl]-3,4-dihydro-2H-pyrrol-5-amine

Compound 33

To a solution of 5-methoxy-3,4-dihydro-2H-pyrrole (520 mg) in MeOH (8 mL) was added (1S)-1H-inden-1-amine, 2,3-dihydro (538 mg, 4.04 mmol, CAS 61341-86-4) at room temperature. The mixture was stirred at room temperature for 40 h. The reaction was then cooled to room temperature and concentrated. Flash column chromatography (5% 7N $NH_3$ in MeOH/DCM) yielded (S)—N-(2,3-dihydro-1H-inden-1-yl)-3,4-dihydro-2H-pyrrol-5-amine, as a white solid. $^1$H NMR (300 MHz, $CDCl_3$) δ: 7.30-7.39 (m, 5H), 7.13-7.28 (m, 3H), 5.25-5.38 (m, 1H), 3.72 (t, J=6.7 Hz, 2H), 2.91-3.04 (m, 1H), 2.77-2.91 (m, 1H), 2.54-2.72 (m, 1H), 2.35-2.54 (m, 2H), 1.93-2.10 (m, 2H), 1.76-1.91 (m, 1H).

Compounds 34 to 37 were prepared in a similar manner to the method described in Example 7 for Compound 33. The reagents used and the results obtained are tabulated below in Table 6.

TABLE 6

| Compound Number | IUPAC Name | Starting material | $^1$H NMR (Solvent) δ ppm |
|---|---|---|---|
| 34 | N-[(1S)-1,2,3,4-Tetrahydronaphthalen-1-yl]-3,4-dihydro-2H-pyrrol-5-amine | 1-Naphthalenamine, 1,2,3,4-tetrahydro-, (1S)- (CAS 23357-52-0) | ($CDCl_3$) 7.32-7.40 (m, 1H), 7.13-7.20 (m, 2H), 7.05-7.12 (m, 1H), 4.99 (t, J = 5.1 Hz, 1H), 3.73 (t, J = 6.7 Hz, 2H), 2.65-2.90 (m, 2H), 2.35-2.54 (m, 2H), 1.73-2.13 (m, 6H). |
| 35 | N-(7-Fluoro-2,3-dihydro-1H-inden-1-yl)-3,4-dihydro-2H-pyrrol-5-amine | 1H-Inden-1-amine, 7-fluoro-2,3-dihydro (CAS 1071449-14-3) | ($CD_3OD$) 7.36 (td, J = 7.8, 5.3 Hz, 1H), 7.15 (d, J =7.6 Hz, 1H), 6.93-7.02 (m, 1H), 5.28 (dd, J = 7.6, 4.4 Hz, 1H), 3.79 (t, J = 7.0 Hz, 2H), 3.08-3.24 (m, 1H), 2.93-3.05 (m, 1H), 2.83-2.91 (m, 2H), 2.51-2.71 (m, 1H), 2.25 (quin, J = 7.6 Hz, 2H), 2.06-2.18 (m, 1H). |
| 36 | N-(3,4-Dihydro-2H-pyrrol-5-yl)-5-methyl-3,4-dihydro-2H-1,4-benzoxazin-6-amine | 2H-1,4-Benzoxazin-6-amine, 3,4-dihydro-5-methyl CAS 850560-41-7 | ($CD_3OD$) 6.51 (d, J = 8.5 Hz, 1H), 6.19 (d, J = 8.5 Hz, 1H), 4.06-4.14 (m, 2H), 3.35-3.40 (m, 4H), 2.52 (t, J = 7.9 Hz, 2H), 1.95-2.10 (m, 2H), 1.91 (s, 3H). |
| 37 | N-[(1S)-4-Methyl-2,3-dihydro-1H-inden-1-yl]-3,4-dihydro-2H-pyrrol-5-amine | (S)-4-methyl-2,3-dihydro-1H-inden-1-amine CAS 1071448-91-3 | ($CD_3OD$) 6.96-7.15 (m, 3H), 5.15 (t, J = 7.3 Hz, 1H), 3.62 (t, J = 6.9 Hz, 2H), 2.86-3.00 (m, 1H), 2.66-2.80 (m, 1H), 2.44-2.62 (m, 3H), 1.91-2.05 (m, 2H), 1.72-1.89 (m, 1H). |

EXAMPLE 8

4-Methyl-N-[(2E)-pyrrolidin-2-ylidene]-1H-pyrrolo[2,3-b]pyridin-5-amine

Compound 38

To a solution of tetrabutylammonium nitrate (2.48 g, 8.0 mmol) in DCM (30 mL) was added trifluoroacetic anhydride (1.68 g, 8.0 mmol) at 0° C. under argon. Then 4-methyl-1-(phenylsulfonyl)-1H-pyrrolo[2,3-b]pyridine, (1.2 g, 4.42 mmol) (CAS 1227270-73-6) in anhydrous DCM (20 mL) was added slowly to the above reaction mixture at 0° C. The mixture was stirred at 0° C. for 1.5 h. The reaction was quenched with water and extracted in dichloromethane. The dichloromethane layer was dried ($MgSO_4$) filtered, concentrated and purified by MPLC (solid load) using hexane:EtOAc (8:2) gave 4-methyl-5-nitro-1-(phenylsulfonyl)-1H-pyrrolo[2,3-b]pyridine. $^1$H NMR (300 MHz, $CD_3OD$) δ: 8.95 (s, 1H), 8.18 (d, J=8.2 Hz, 2H), 8.00 (d, J=4.1 Hz, 1H), 7.64-7.74 (m, 1H), 7.53-7.64 (m, 2H), 7.02 (d, J=4.1 Hz, 1H), 2.77 (s, 3H).

To a mixture of 4-methyl-5-nitro-1-(phenylsulfonyl)-1H-pyrrolo[2,3-b]pyridine, (410 mg, 1.29 mmol) in THF (15 mL) and EtOH (10 mL) was added 10% palladium on carbon (10 wt % of Pd/C; 45 mg) under argon. The mixture was hydrogenated using a hydrogen balloon at room temperature for 16 hours. The reaction mixture was flushed with nitrogen and filtered through a plug of Celite® and concentrated in vacuo. The crude material was purified by flash column chromatography on silica gel using hexane:EtOAc (4:6) to get 4-methyl-1-(phenylsulfonyl)-1H-pyrrolo[2,3-b]pyridin-5-amine, (370 mg). $^1$H NMR (300 MHz, $CD_3OD$) δ: 7.96-8.04 (m, 2H), 7.83 (s, 1H), 7.53-7.64 (m, 2H), 7.42-7.52 (m, 2H), 6.65 (d, J=4.1 Hz, 1H), 2.26 (s, 3H).

A solution of 4-methyl-1-(phenylsulfonyl)-1H-pyrrolo[2,3-b]pyridin-5-amine, (775 mg, 2.7 mmol) and 5-(methylthio)-3,4-dihydro-2H-pyrrole (345 mg) in i-PrOH (14 mL) was heated at 105° C. for 3 days. The refluxed mixture was then cooled to room temperature and concentrated. Flash column chromatography (4-6% 7N $NH_3$ in MeOH/DCM) yielded N-(3,4-dihydro-2H-pyrrol-5-yl)-4-methyl-1-(phenylsulfonyl)-1H-pyrrolo[2,3-b]pyridin-5-amine, (180 mg) $^1$H NMR (300 MHZ, $CD_3OD$) δ: 8.10 (d, J=7.6 Hz, 2H), 7.89 (s, 1H), 7.75 (d, J=4.1 Hz, 1H), 7.63 (s, 1H), 7.54 (d, J=8.2 Hz, 2H), 6.77 (d, J=4.1 Hz, 1H), 2.63 (s, 2H), 2.09 (t, J=7.5 Hz, 3H).

A mixture of N-(3,4-dihydro-2H-pyrrol-5-yl)-4-methyl-1-(phenylsulfonyl)-1H-pyrrolo[2,3-b]pyridin-5-amine, (180 mg) in MeOH (10 mL) was added 5N aq. solution of NaOH (2 mL) and the mixture was heated at 80° C. for 4 h. Cooled to room temperature a white solid precipitated, which was filtered off. Silica gel was added to the filtrate and concentrated. This material was purified by using silica gel column chromatography (5% 7N $NH_3$ in MeOH/DCM) gave the title compound, (43 mg). $^1$H NMR (300 MHz, CD$_3$OD) δ: 7.75 (s, 1H), 7.29 (d, J=3.5 Hz, 1H), 6.47 (d, J=3.2 Hz, 1H), 3.38 (t, J=6.7 Hz, 2H), 2.60 (t, J=7.6 Hz, 2H), 2.37 (s, 3H), 2.08 (quin, J=7.4 Hz, 2H).

EXAMPLE 9

In Vitro Activity

The compounds described herein were tested for alpha adrenergic activity using a Fluorometric Imaging plate Reader (FLIPR) assay (Princen et al., 2003, Cytometry Part A. 51, pp. 35-45). Cells are loaded into a plate reader with a Ca$^{2+}$ dye indicator and incubated with various compounds. This assay is adequate for monitoring the intracellular Ca$^{2+}$ mobilization from fluorescent readings to evaluate receptor agonists. The compounds activity is expressed as EC$_{50}$ (nanomolar concentration that elicits a half-maximal response) and their relative efficacy compared to a standard full agonist (see Table 7 below). The compounds described herein activate alpha adrenergic receptors.

TABLE 7

| Compound number | IUPAC Name | Alpha 2A | Alpha 2B | Alpha 2C |
|---|---|---|---|---|
| 1 | N-1-Naphthyl-3,4-dihydro-2H-pyrrol-5-amine | 61 (0.81) | 30 (0.16) | 5 (0.88) |
| 2 | N-(2-Methyl-1-naphthyl)-3,4-dihydro-2H-pyrrol-5-amine | 733 (0.61) | 145 (0.18) | 368 (0.85) |
| 3 | N-(4-Bromo-1-naphthyl)-3,4-dihydro-2H-pyrrol-5-amine | n/a | 700 (0.15) | 833 (0.85) |
| 4 | N-(3,4-Dihydro-2H-pyrrol-5-yl)-1H-benzimidazol-5-amine | n/a | 714 (0.19) | 142 (1.06) |
| 5 | N-(3,4-Dihydro-2H-pyrrol-5-yl)-6,7-dihydro-5H-cyclopenta[b]pyridin-3-amine | n/a | n/a | 1282 (0.86) |
| 6 | 4-Chloro-N-[(2E)-pyrrolidin-2-ylidene]-1,5-naphthyridin-3-amine | n/a | n/a | 2597 (0.59) |
| 7 | N-(4-Chloro-1-naphthyl)-3,4-dihydro-2H-pyrrol-5-amine | n/a | 1070 (0.33) | 672 (0.84) |
| 8 | 5-Bromo-N-(3,4-dihydro-2H-pyrrol-5-yl)quinoxalin-6-amine | 1069 (0.81) | 2203 (0.21) | 1051 (0.82) |
| 9 | 8-Chloro-N-(3,4-dihydro-2H-pyrrol-5-yl)quinolin-7-amine | 429 (1) | 1049 (0.38) | 218 (0.97) |
| 10 | 4-Bromo-N-(3,4-dihydro-2H-pyrrol-5-yl)-1H-benzimidazol-5-amine | 3 (1) | 90 (0.76) | 1.5 (0.94) |
| 11 | 4-Chloro-N-(3,4-dihydro-2H-pyrrol-5-yl)-1H-benzimidazol-5-amine | 216 (0.98) | 513 (0.69) | 35 (1) |
| 12 | N-(3,4-dihydro-2H-pyrrol-5-yl)-4-methyl-1H-benzimidazol-5-amine | 203 (1) | 510 (0.86) | 58 (1) |
| 13 | 7-Chloro-N-(3,4-dihydro-2H-pyrrol-5-yl)-1H-benzimidazol-5-amine | n/a | 1838 (0.35) | 435 (0.98) |
| 14 | N-(3,4-Dihydro-2H-pyrrol-5-yl)quinoxalin-6-amine | n/a | n/a | 2737 (0.66) |
| 15 | N-(5,6,7,8-Tetrahydronaphthalen-2-yl)-3,4-dihydro-2H-pyrrol-5-amine | n/a | 293 (0.14) | 37 (0.93) |
| 16 | N-(2,3-Dihydro-1H-inden-4-yl)-3,4-dihydro-2H-pyrrol-5-amine | n/a | n/a | 123 (0.85) |
| 17 | N-(3,4-Dihydro-2H-pyrrol-5-yl)-1H-indol-5-amine | n/a | 10 (0.15) | 9 (0.9) |
| 18 | N-(3,4-Dihydro-2H-pyrrol-5-yl)-4-methyl-1H-indol-5-amine | n/a | 39 (0.18) | 69 (0.9) |
| 19 | N-(3,4-Dihydro-2H-pyrrol-5-yl)-7-methyl-1H-indol-5-amine | n/a | 142 (0.29) | 12 (0.85) |
| 20 | 7-Bromo-N-(3,4-dihydro-2H-pyrrol-5-yl)-1H-indol-5-amine | n/a | 79 (0.61) | 12 (0.95) |
| 21 | N-(3,4-Dihydro-2H-pyrrol-5-yl)-1H-indol-6-amine | n/a | n/a | 280 (0.75) |
| 22 | N-(3,4-Dihydro-2H-pyrrol-5-yl)-1H-indol-7-amine | n/a | n/a | 2161 (0.61) |
| 23 | N-1-Benzothien-5-yl-3,4-dihydro-2H-pyrrol-5-amine | n/a | n/a | 89 (0.66) |
| 24 | N-1-Benzofuran-5-yl-3,4-dihydro-2H-pyrrol-5-amine | n/a | n/a | 630 (0.51) |
| 25 | N-(3,4-Dihydro-2H-pyrrol-5-yl)-1H-indol-4-amine | 115 (0.7) | 152 (0.42) | <10 (0.99) |
| 26 | N-[(2E)-Pyrrolidin-2-ylidene]-1H-pyrrolo[2,3-b]pyridin-5-amine | 118 (0.85) | 17 (0.96) | 6 (0.97) |
| 27 | N-(3,4-Dihydro-2H-pyrrol-5-yl)-5-methylquinoxalin-6-amine fumarate | 121 (0.89) | n/a | 16 (0.9) |
| 28 | N-(3,4-Dihydro-2H-pyrrol-5-yl)quinolin-7-amine | n/a | n/a | 104 (0.96) |
| 29 | N-(3,4-Dihydro-2H-pyrrol-5-yl)-8-methylquinolin-7-amine | 6 (0.98) | 80 (0.2) | <1 (1) |
| 30 | N-(3,4-dihydro-2H-pyrrol-5-yl)quinolin-8-amine | n/a | n/a | 2974 (0.71) |
| 31 | 4-Bromo-N-(3,4-dihydro-2H-pyrrol-5-yl)-1,3-benzothiazol-5-amine | 96 (.98) | 117 (.76) | 25 (.92) |

TABLE 7-continued

| Compound number | IUPAC Name | Alpha 2A | Alpha 2B | Alpha 2C |
|---|---|---|---|---|
| 32 | N-(3,4-Dihydro-2H-pyrrol-5-yl)isoquinolin-8-amine | n/a | n/a | 643 (0.95) |
| 33 | N-[(1S)-2,3-Dihydro-1H-inden-1-yl]-3,4-dihydro-2H-pyrrol-5-amine | n/a | n/a | 281 (0.68) |
| 34 | N-[(1S)-1,2,3,4-Tetrahydronaphthalen-1-yl]-3,4-dihydro-2H-pyrrol-5-amine | n/a | 163 (0.43) | 221 (0.8) |
| 35 | N-(7-Fluoro-2,3-dihydro-1H-inden-1-yl)-3,4-dihydro-2H-pyrrol-5-amine | n/a | 618 (0.44) | 560 (0.87) |
| 36 | N-(3,4-Dihydro-2H-pyrrol-5-yl)-5-methyl-3,4-dihydro-2H-1,4-benzoxazin-6-amine | 583 (0.68) | 579 (0.77) | 327 (0.87) |
| 37 | N-[(1S)-4-Methyl-2,3-dihydro-1H-inden-1-yl]-3,4-dihydro-2H-pyrrol-5-amine | 272 (0.43) | 21 (0.9) | 58 (0.94) |
| 38 | 4-Methyl-N-[(2E)-pyrrolidin-2-ylidene]-1H-pyrrolo[2,3-b]pyridin-5-amine | 555 (0.79) | n/a | 22 (0.9) |

Potency (nM);
efficacy ($EC_{50}$);
n/a: not available.

EXAMPLE 10

In-Vivo Intraoccular Pressure Compound Screening

The experimental animals used, were Normotensive male Dutch-Belted rabbits over 6 months in age (n=4/compound/dose screened). A single drop (50 µl) of the drug formulation, which yields 0.15% or 1.0% of the active metabolite was administered topically by pipette onto the right eye (treated eye) at approximately 0700 hours. Intraoccular Pressure (IOP) of the rabbits (treated and untreated eyes) was measured 0 hours before and at 0.5, 1, 2, 3, 4, 6 and 8 hours after topical eyedrop administration. IOP at the time of eyedrop administration (0 hours) was used as a baseline value. Prior to the tonometric measurements, 0.05% proparacaine (50 µl) was administered to each eye. Tonometric IOP measurements were obtained with a Mentor Pneumontonmeter. Additionally, all studies were masked. At least 1 week of wash-out time was allowed for each rabbit between dosings. All animals were examined for sedation, ocular irritation, and changes in pupil diameter throughout the course of the experiments. Compounds 9, 10, 11, 12, 27, 29 show potential in lowering IOP. In this assay, Compound 10 lowered IOP about 35%.

We claim:

1. A compound having formula I, its enantiomers, diastereoisomers, tautomers or a pharmaceutically acceptable salt thereof

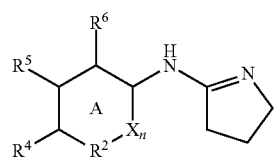

Formula I wherein:
n is 0 or 1;
A is an aromatic or non-aromatic ring;
X is N, N—$R^1$, CH—$R^1$, C—$R^1$;
$R^1$ is H, $C_{1-6}$ alkyl or halogen;
$R^2$ is N, N—$R^3$, CH—$R^3$, C—$R^3$, O or S;
$R^3$ is H, halogen, or $C_{1-6}$ alkyl;
$R^4$ is halogen, H, $C_{1-6}$ alkyl or part of a ring as a S, O, N or as a C;
$R^5$ is a S, N or is a C and is always part of a ring;
$R^6$ is H, $C_{1-6}$ alkyl, halogen or is part of a ring as a S, O, N or as a C;
$R^4$ and $R^5$ can form a 5 or 6 membered carbo- or heterocyclic ring, aromatic or non-aromatic, optionally substituted with 1 to 2 $C_{1-6}$ alkyl or with 1 to 2 halogen and is directly attached to the rest of the molecule; or
$R^5$ and $R^6$ can form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule;
except (+/−) 3,4-dihydro-N-(1,2,3,4-tetrahydro-1-naphthalenyl)-2H-pyrrol-5-amine.

2. A compound according to claim 1 of formula II

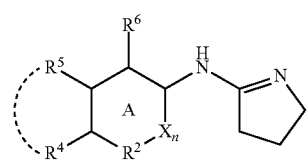

Formula II wherein:
n is 1;
A is an aromatic ring;
X is C—$R^1$;
$R^1$ is H;
$R^2$ is N or C—$R^3$;
$R^3$ is H, halogen, or $C_{1-6}$ alkyl;
$R^4$ is part of a ring as a S, O, N or as a C;
$R^5$ is a N or is a C and is always part of a ring;
$R^6$ is H, $C_{1-6}$ alkyl or halogen; and
$R^4$ and $R^5$ form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule.

3. A compound according to claim 1 of formula III

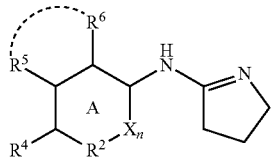

Formula III wherein:
n is 1;
A is an aromatic ring;
X is C—$R^1$;
$R^1$ is H, $C_{1-3}$ alkyl
$R^2$ is N or C—$R^3$,
$R^3$ is H, halogen, or $C_{1-6}$ alkyl;
$R^4$ is halogen or H;
$R^5$ is a N or C and is always part of a ring;
$R^6$ is part of a ring as a N or as a C;
$R^5$ and $R^6$ form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule.

4. A compound according to claim 1 of formula IV

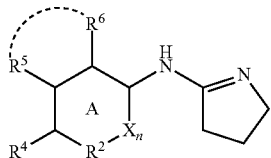

Formula IV wherein:
n is 0;
A is a non-aromatic ring;
$R^2$ is CH—$R^3$;
$R^3$ is H;
$R^4$ is H;
$R^5$ is C and is always part of a ring;
$R^6$ is part of a ring as a C; and
$R^5$ and $R^6$ form a 6 membered aromatic carbocyclic ring directly attached to the rest of the molecule.

5. A compound according to claim 1 of formula V

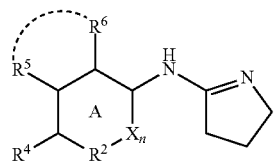

Formula V wherein
n is 1;
A is a non-aromatic ring;
X is CH—$R^1$;
$R^1$ is H;
$R^2$ is CH—$R^3$;
$R^3$ is H;
$R^4$ is H;
$R^5$ is C and is always part of a ring;
$R^6$ is part of a ring as a C; and
$R^5$ and $R^6$ form a 6 membered aromatic carbocyclic ring, optionally substituted with $C_{1-6}$ alkyl or halogen and is directly attached to the rest of the molecule;
except (+/−) 3,4-dihydro-N-(1,2,3,4-tetrahydro-1-naphthalenyl)-2H-pyrrol-5-amine.

6. A compound according to claim 1 selected from the group consisting of:
N-1-Naphthyl-3,4-dihydro-2H-pyrrol-5-amine;
N-(2-Methyl-1-naphthyl)-3,4-dihydro-2H-pyrrol-5-amine;
N-(4-Bromo-1-naphthyl)-3,4-dihydro-2H-pyrrol-5-amine;
N-(3,4-Dihydro-2H-pyrrol-5-yl)-1H-benzimidazol-5-amine;
N-(3,4-Dihydro-2H-pyrrol-5-yl)-6,7-dihydro-5H-cyclopenta[b]pyridin-3-amine;
4-Chloro-N-[(2E)-pyrrolidin-2-ylidene]-1,5-naphthyridin-3-amine;
N-(4-Chloro-1-naphthyl)-3,4-dihydro-2H-pyrrol-5-amine fumarate;
N-(4-Chloro-1-naphthyl)-3,4-dihydro-2H-pyrrol-5-amine;
5-Bromo-N-(3,4-dihydro-2H-pyrrol-5-yl)quinoxalin-6-amine fumarate;
5-Bromo-N-(3,4-dihydro-2H-pyrrol-5-yl)quinoxalin-6-amine;
8-Chloro-N-(3,4-dihydro-2H-pyrrol-5-yl)quinolin-7-amine;
4-Bromo-N-(3,4-dihydro-2H-pyrrol-5-yl)-1H-benzimidazol-5-amine;
4-Chloro-N-(3,4-dihydro-2H-pyrrol-5-yl)-1H-benzimidazol-5-amine;
N-(3,4-dihydro-2H-pyrrol-5-yl)-4-methyl-1H-benzimidazol-5-amine;
7-Chloro-N-(3,4-dihydro-2H-pyrrol-5-yl)-1H-benzimidazol-5-amine;
N-(3,4-Dihydro-2H-pyrrol-5-yl)quinoxalin-6-amine;
N-(5,6,7,8-Tetrahydronaphthalen-2-yl)-3,4-dihydro-2H-pyrrol-5-amine;
N-(2,3-Dihydro-1H-inden-4-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;
7-Bromo-N-(3,4-Dihydro-2H-pyrrol-5-yl)-1H-indol-5-amine;
N-(3,4-Dihydro-2H-pyrrol-5-yl)-1H-indol-6-amine;
N-(3,4-Dihydro-2H-pyrrol-5-yl)-1H-indol-7-amine;
N-1-Benzothien-5-yl-3,4-dihydro-2H-pyrrol-5-amine;
N-1-Benzofuran-5-yl-3,4-dihydro-2H-pyrrol-5-amine;
N-(3,4-Dihydro-2H-pyrrol-5-yl)-1H-indol-4-amine;
N-[(2E)-Pyrrolidin-2-ylidene]-1H-pyrrolo[2,3-b]pyridin-5-amine;
N-(3,4-Dihydro-2H-pyrrol-5-yl)-5-methylquinoxalin-6-amine fumarate;
N-(3,4-Dihydro-2H-pyrrol-5-yl)-5-methylquinoxalin-6-amine;
N-(3,4-Dihydro-2H-pyrrol-5-yl)quinolin-7-amine;
N-(3,4-Dihydro-2H-pyrrol-5-yl)-8-methylquinolin-7-amine;
N-(3,4-Dihydro-2H-pyrrol-5-yl)-8-methylquinolin-7-amine fumarate;
N-(3,4-dihydro-2H-pyrrol-5-yl)quinolin-8-amine;

4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-(3,4-Dihydro-2H-pyrrol-5-yl)isoquinolin-8-amine fumarate;
N-(3,4-Dihydro-2H-pyrrol-5-yl)isoquinolin-8-amine;
N-[(1S)-2,3-Dihydro-1H-inden-1-yl]-3,4-dihydro-2H-pyrrol-5-amine;
N-[(1S)-1,2,3,4-Tetrahydronaphthalen-1-yl]-3,4-dihydro-2H-pyrrol-5-amine;
N-(7-Fluoro-2,3-dihydro-1H-inden-1-yl)-3,4-dihydro-2H-pyrrol-5-amine;
N-(3,4-Dihydro-2H-pyrrol-5-yl)-5-methyl-3,4-dihydro-2H-1,4-benzoxazin-6-amine;
N-[(1S)-4-Methyl-2,3-dihydro-1H-inden-1-yl]-3,4-dihydro-2H-pyrrol-5-amine;
4-Methyl-N-[(2E)-pyrrolidin-2-ylidene]-1H-pyrrolo[2,3-b]pyridin-5-amine.

7. A compound according to claim 1 selected from the group consisting of:
N-1-Naphthyl-3,4-dihydro-2H-pyrrol-5-amine;
N-(3,4-Dihydro-2H-pyrrol-5-yl)-1H-benzimidazol-5-amine;
4-Bromo-N-(3,4-dihydro-2H-pyrrol-5-yl)-1H-benzimidazol-5-amine;
N-(5,6,7,8-Tetrahydronaphthalen-2-yl)-3,4-dihydro-2H-pyrrol-5-amine;
N-(2,3-Dihydro-1H-inden-4-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;
7-Bromo-N-(3,4-dihydro-2H-pyrrol-5-yl)-1H-indol-5-amine;
N-(3,4-Dihydro-2H-pyrrol-5-yl)-1H-indol-6-amine;
N-1-Benzothien-5-yl-3,4-dihydro-2H-pyrrol-5-amine;
N-(3,4-Dihydro-2H-pyrrol-5-yl)-1H-indol-4-amine;
N-[(2E)-Pyrrolidin-2-ylidene]-1H-pyrrolo[2,3-b]pyridin-5-amine;
N-(3,4-Dihydro-2H-pyrrol-5-yl)-5-methylquinoxalin-6-amine fumarate;
N-(3,4-Dihydro-2H-pyrrol-5-yl)-5-methylquinoxalin-6-amine;
N-(3,4-Dihydro-2H-pyrrol-5-yl)quinolin-7-amine;
N-(3,4-Dihydro-2H-pyrrol-5-yl)-8-methylquinolin-7-amine;
N-(3,4-Dihydro-2H-pyrrol-5-yl)-8-methylquinolin-7-amine fumarate;
4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-[(1S)-2,3-Dihydro-1H-inden-1-yl]-3,4-dihydro-2H-pyrrol-5-amine;
N-[(1S)-1,2,3,4-Tetrahydronaphthalen-1-yl]-3,4-dihydro-2H-pyrrol-5-amine.

8. A compound according to claim 1 selected from the group consisting of:
4-Bromo-N-(3,4-dihydro-2H-pyrrol-5-yl)-1H-benzimidazol-5-amine;
N-(5,6,7,8-Tetrahydronaphthalen-2-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;
7-Bromo-N-(3,4-dihydro-2H-pyrrol-5-yl)-1H-indol-5-amine;
N-1-Benzothien-5-yl-3,4-dihydro-2H-pyrrol-5-amine;
N-(3,4-Dihydro-2H-pyrrol-5-yl)-8-methylquinolin-7-amine fumarate;
4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-(3,4-Dihydro-2H-pyrrol-5-yl)-8-methylquinolin-7-amine.

9. A pharmaceutical composition comprising at least one compound of having formula I:

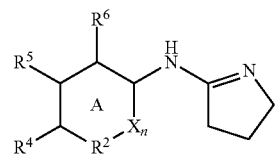

Formula I wherein:
n is 0 or 1;
A is an aromatic or non-aromatic ring;
X is N, N—$R^1$, CH—$R^1$, C—$R^1$;
$R^1$ is H, $C_{1-6}$ alkyl or halogen;
$R^2$ is N, N—$R^3$, CH—$R^3$, C—$R^3$, O or S;
$R^3$ is H, halogen, or $C_{1-6}$ alkyl;
$R^4$ is halogen, H, $C_{1-6}$ alkyl or part of a ring as a S, O, N or as a C;
$R^5$ is a S, N or is a C and is always part of a ring;
$R^6$ is H, $C_{1-6}$ alkyl, halogen or is part of a ring as a S, O, N or as a C;
$R^4$ and $R^5$ can form a 5 or 6 membered carbo- or heterocyclic ring, aromatic or non-aromatic, optionally substituted with 1 to 2 $C_{1-6}$ alkyl or with 1 to 2 halogen and is directly attached to the rest of the molecule; or
$R^5$ and $R^6$ can form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule;
except (+/−) 3,4-dihydro-N-(1,2,3,4-tetrahydro-1-naphthalenyl)-2H-pyrrol-5-amine;
and a pharmaceutically acceptable carrier.

10. The pharmaceutical composition of claim 9, comprising at least one compound of formula II:

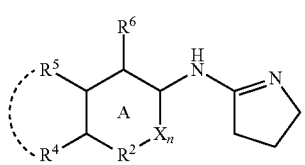

Formula II wherein:
n is 1;
A is an aromatic ring;
X is C—$R^1$;
$R^1$ is H;

$R^2$ is N or C—$R^3$;
$R^3$ is H, halogen, or $C_{1-6}$ alkyl;
$R^4$ is part of a ring as a S, O, N or as a C;
$R^5$ is a N or is a C and is always part of a ring;
$R^6$ is H, $C_{1-6}$ alkyl or halogen; and
$R^4$ and $R^5$ form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule.

11. The pharmaceutical composition of claim 9, comprising at least one compound of formula III:

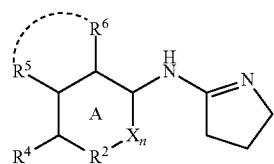

Formula III wherein:
n is 1;
A is an aromatic ring;
X is C—$R^1$;
$R^1$ is H, $C_{1-3}$ alkyl;
$R^2$ is N or C—$R^3$, $R^3$ is H, halogen, or $C_{1-6}$ alkyl;
$R^4$ is halogen or H;
$R^5$ is a N or C and is always part of a ring;
$R^6$ is part of a ring as a N or as a C;
$R^5$ and $R^6$ form a 5 or 6 membered carbo- or heterocyclic ring, aromatic or non-aromatic, optionally substituted with 1 to 2 $C_{1-6}$ alkyl or 1 to 2 halogen and is directly attached to the rest of the molecule.

12. The pharmaceutical composition of claim 9, comprising at least one compound of formula IV:

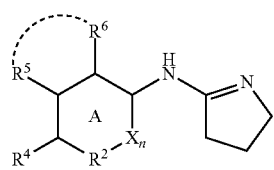

Formula IV wherein:
n is 0;
A is a non-aromatic ring;
$R^2$ is CH—$R^3$;
$R^3$ is H;
$R^4$ is H;
$R^5$ is C and is always part of a ring;
$R^6$ is part of a ring as a C; and
$R^5$ and $R^6$ form a 6 membered aromatic carbocyclic ring directly attached to the rest of the molecule.

13. The pharmaceutical composition of claim 9, comprising at least one compound of formula V:

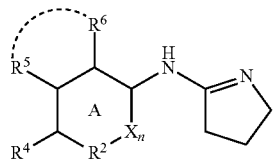

Formula V wherein
n is 1;
A is a non-aromatic ring;
X is CH—$R^1$;
$R^1$ is H;
$R^2$ is CH—$R^3$;
$R^3$ is H;
$R^4$ is H;
$R^5$ is C and is always part of a ring;
$R^6$ is part of a ring as a C; and
$R^5$ and $R^6$ form a 6 membered aromatic carbocyclic ring, optionally substituted with $C_{1-6}$ alkyl or halogen and is directly attached to the rest of the molecule;
except (+/−) 3,4-dihydro-N-(1,2,3,4-tetrahydro-1-naphthalenyl)-2H-pyrrol-5-amine.

14. The pharmaceutical composition of claim 9, comprising at least one compound selected from the group consisting of:
N-1-Naphthyl-3,4-dihydro-2H-pyrrol-5-amine;
N-(2-Methyl-1-naphthyl)-3,4-dihydro-2H-pyrrol-5-amine;
N-(4-Bromo-1-naphthyl)-3,4-dihydro-2H-pyrrol-5-amine;
N-(3,4-Dihydro-2H-pyrrol-5-yl)-1H-benzimidazol-5-amine;
N-(3,4-Dihydro-2H-pyrrol-5-yl)-6,7-dihydro-5H-cyclopenta[b]pyridin-3-amine;
4-Chloro-N-[(2E)-pyrrolidin-2-ylidene]-1,5-naphthyridin-3-amine;
N-(4-Chloro-1-naphthyl)-3,4-dihydro-2H-pyrrol-5-amine fumarate;
N-(4-Chloro-1-naphthyl)-3,4-dihydro-2H-pyrrol-5-amine;
5-Bromo-N-(3,4-dihydro-2H-pyrrol-5-yl)quinoxalin-6-amine fumarate;
5-Bromo-N-(3,4-dihydro-2H-pyrrol-5-yl)quinoxalin-6-amine;
8-Chloro-N-(3,4-dihydro-2H-pyrrol-5-yl)quinolin-7-amine;
4-Bromo-N-(3,4-dihydro-2H-pyrrol-5-yl)-1H-benzimidazol-5-amine;
4-Chloro-N-(3,4-dihydro-2H-pyrrol-5-yl)-1H-benzimidazol-5-amine;
N-(3,4-dihydro-2H-pyrrol-5-yl)-4-methyl-1H-benzimidazol-5-amine;
7-Chloro-N-(3,4-dihydro-2H-pyrrol-5-yl)-1H-benzimidazol-5-amine;
N-(3,4-Dihydro-2H-pyrrol-5-yl)quinoxalin-6-amine;
N-(5,6,7,8-Tetrahydronaphthalen-2-yl)-3,4-dihydro-2H-pyrrol-5-amine;
N-(2,3-Dihydro-1H-inden-4-yl)-3,4-dihydro-2H-pyrrol-5-amine;
N-(3,4-Dihydro-2H-pyrrol-5-yl)-1H-indol-5-amine;
N-(3,4-Dihydro-2H-pyrrol-5-yl)-4-methyl-1H-indol-5-amine;
N-(3,4-Dihydro-2H-pyrrol-5-yl)-7-methyl-1H-indol-5-amine;

7-Bromo-N-(3,4-dihydro-2H-pyrrol-5-yl)-1H-indol-5-amine;
N-(3,4-Dihydro-2H-pyrrol-5-yl)-1H-indol-6-amine;
N-(3,4-Dihydro-2H-pyrrol-5-yl)-1H-indol-7-amine;
N-1-Benzothien-5-yl-3,4-dihydro-2H-pyrrol-5-amine;
N-1-Benzofuran-5-yl-3,4-dihydro-2H-pyrrol-5-amine;
N-(3,4-Dihydro-2H-pyrrol-5-yl)-1H-indol-4-amine;
N-[(2E)-Pyrrolidin-2-ylidene]-1H-pyrrolo[2,3-b]pyridin-5-amine;
N-(3,4-Dihydro-2H-pyrrol-5-yl)-5-methylquinoxalin-6-amine fumarate;
N-(3,4-Dihydro-2H-pyrrol-5-yl)-5-methylquinoxalin-6-amine;
N-(3,4-Dihydro-2H-pyrrol-5-yl)quinolin-7-amine;
N-(3,4-Dihydro-2H-pyrrol-5-yl)-8-methylquinolin-7-amine;
N-(3,4-Dihydro-2H-pyrrol-5-yl)-8-methylquinolin-7-amine fumarate;
N-(3,4-dihydro-2H-pyrrol-5-yl)quinolin-8-amine;
4-Bromo-N-(3,4-dihydro-2H-pyrrol-5-yl)-1,3-benzothiazol-5-amine fumarate;
4-Bromo-N-(3,4-dihydro-2H-pyrrol-5-yl)-1,3-benzothiazol-5-amine;
N-(3,4-Dihydro-2H-pyrrol-5-yl)isoquinolin-8-amine fumarate;
N-(3,4-Dihydro-2H-pyrrol-5-yl)isoquinolin-8-amine;
N-[(1S)-2,3-Dihydro-1H-inden-1-yl]-3,4-dihydro-2H-pyrrol-5-amine;
N-[(1S)-1,2,3,4-Tetrahydronaphthalen-1-yl]-3,4-dihydro-2H-pyrrol-5-amine;
N-(7-Fluoro-2,3-dihydro-1H-inden-1-yl)-3,4-dihydro-2H-pyrrol-5-amine;
N-(3,4-Dihydro-2H-pyrrol-5-yl)-5-methyl-3,4-dihydro-2H-1,4-benzoxazin-6-amine;
N-[(1S)-4-Methyl-2,3-dihydro-1H-inden-1-yl]-3,4-dihydro-2H-pyrrol-5-amine;
4-Methyl-N-[(2E)-pyrrolidin-2-ylidene]-1H-pyrrolo[2,3-b]pyridin-5-amine.

\* \* \* \* \*